(12) United States Patent
Holland et al.

(10) Patent No.: US 11,547,778 B2
(45) Date of Patent: Jan. 10, 2023

(54) SYSTEMS AND METHODS FOR PREPARING CORNEAL TISSUE FOR IMPLANT

(71) Applicant: CorneaGen Inc., Seattle, WA (US)

(72) Inventors: Edward J. Holland, Union, KY (US); Kevin Potts, Lexington, NC (US); Timothy G. Baldwin, Winston-Salem, NC (US)

(73) Assignee: CORNEAGEN INC., Seattle, WA (US)

( * ) Notice: Subject to any disclaimer, the term of this patent is extended or adjusted under 35 U.S.C. 154(b) by 234 days.

(21) Appl. No.: 16/800,059

(22) Filed: Feb. 25, 2020

(65) Prior Publication Data

US 2020/0268941 A1 Aug. 27, 2020

Related U.S. Application Data

(60) Provisional application No. 62/810,351, filed on Feb. 25, 2019.

(51) Int. Cl.
*A61L 27/36* (2006.01)
*A61F 2/14* (2006.01)
*A61F 9/007* (2006.01)
*A61F 9/013* (2006.01)

(52) U.S. Cl.
CPC .......... *A61L 27/3691* (2013.01); *A61F 2/142* (2013.01); *A61L 27/3604* (2013.01); *A61F 9/007* (2013.01); *A61F 9/0133* (2013.01); *A61L 2430/16* (2013.01)

(58) Field of Classification Search
None
See application file for complete search history.

(56) References Cited

PUBLICATIONS

Anshu A, et al. Risk of corneal transplant rejection significantly reduced with Descemet's membrane endothelial keratoplasty. Ophthalmology. 2012; 119:536-540.
Busin M, et al. Does thickness matter: ultrathin Descemet stripping automated endothelial keratoplasty. Curr Opin Ophthalmol. 2014; 25:312-318.
Busin M, et al. Microkeratome-assisted preparation of ultrathin grafts for Descemet stripping automated endothelial keratoplasty. Invest Ophthalmol Vis Sci. 2012; 53:521-524.
(Continued)

*Primary Examiner* — Javier G Blanco
(74) *Attorney, Agent, or Firm* — Polsinelli PC

(57) ABSTRACT

A technique can consistently achieve thicknesses of ≤50 μm for corneal tissue for Descemet stripping automated endothelial keratoplasty (DSAEK). Grafts with thicknesses of ≤50 μm are also known as nanothin DSAEK (NT-DSAEK) grafts. Evidence shows that using thinner DSAEK grafts, particularly NT-DSAEK grafts, can significantly improve visual outcomes. According to an example embodiment, a method for producing a corneal graft includes drying a donor cornea to cause a pre-cut thickness of the donor cornea to decrease. The method includes, concurrently with drying the donor cornea, determining pre-cut thickness measurements for the donor cornea. The method includes, in response to the pre-cut thickness measurements indicating the pre-cut thickness of the donor cornea has decreased to a predetermined value, cutting the donor cornea to a post-cut thickness of ≤100 μm, or more particularly ≤50 μm, to produce a corneal graft.

14 Claims, 5 Drawing Sheets

(56) References Cited

PUBLICATIONS

Busin M, et al. Ultrathin Descemet's stripping automated endothelial keratoplasty with the microkeratome double-pass technique: two-year outcomes. Ophthalmology. 2013; 120:1186-1194.

Cheung AY, et al. Technique for preparing ultrathin and nanothin Descemet stripping automated endothelial keratoplasty tissue. Cornea. 2018; 37:661-666.

Choulakian MY, et al. Single-pass microkeratome system for Eye Bank DSAEK tissue preparation: is stromal bed thickness predictable and reproducible? Cornea. 2016; 35:95-99.

Dapena I, et al. Learning curve in Descemet's membrane endothelial keratoplasty: first series of 135 consecutive cases. Ophthalmology. 2011; 118:2147-2154.

Deng SX, et al. Descemet membrane endothelial keratoplasty: safety and outcomes: a report by the american academy of ophthalmology. Ophthalmology. 2018; 125:295-310.

Dickman MM, et al. A randomized multicenter clinical trial of ultrathin Descemet stripping automated endothelial keratoplasty (DSAEK) versus DSAEK. Ophthalmology. 2016; 123:2276-2284.

Droutsas K, et al. Visual outcomes after Descemet membrane endothelial keratoplasty versus Descemet stripping automated endothelial keratoplasty-comparison of specific matched pairs. Cornea. 2016; 35:765-771.

Goldich Y, et al. Contralateral eye comparison of Descemet membrane endothelial keratoplasty and Descemet stripping automated endothelial keratoplasty. Am J Ophthalmol. 2015; 159:155-159.e1.

Guerra FP, et al. Descemet's membrane endothelial keratoplasty: prospective study of 1-year visual outcomes, graft survival, and endothelial cell loss. Ophthalmology. 2011; 118:2368-2373.

Guerra FP, et al. Endothelial keratoplasty: fellow eyes comparison of Descemet stripping automated endothelial keratoplasty and Descemet membrane endothelial keratoplasty. Cornea. 2011; 30:1382-1386.

Hamzaoglu EC, et al. The first 100 eyes of standardized Descemet stripping automated endothelial keratoplasty versus standardized Descemet membrane endothelial keratoplasty. Ophthalmology. 2015; 122:2193-2199.

Hos D, et al. Incidence and clinical course of immune reactions after Descemet membrane endothelial keratoplasty: retrospective analysis of 1000 consecutive eyes. Ophthalmology. 2017; 124:512-518.

Lee WB, et al. Descemet's stripping endothelial keratoplasty: safety and outcomes: a report by the American Academy of Ophthalmology. Ophthalmology. 2009; 116:1818-1830.

Li JY, et al. Graft rejection after Descemet's stripping automated endothelial keratoplasty: graft survival and endothelial cell loss. Ophthalmology. 2012; 119:90-94.

Li JY, et al. Three-year visual acuity outcomes after Descemet's stripping automated endothelial keratoplasty. Ophthalmology. 2012; 119:1126-1129.

Melies GR, et al. Descemet membrane endothelial keratoplasty (DMEK). Cornea. 2006; 25:987-990.

Nahum Y, et al. Graft-recipient collagen lamellar axis discrepancy is compatible with excellent visual acuity after Descemet stripping automated endothelial keratoplasty. Cornea. 2016; 35:938-940.

Nahum Y, et al. Postoperative graft thickness obtained with single-pass microkeratome-assisted ultrathin Descemet stripping automated endothelial keratoplasty. Cornea. 2015; 34:1362-1364.

Neff KD, et al. Comparison of central corneal graft thickness to visual acuity outcomes in endothelial keratoplasty. Cornea. 2011; 30:388-391.

Park CY, et al. Keratoplasty in the United States: a 10-year review from 2005 through 2014. Ophthalmology. 2015; 122: 2432-2442.

Peraza-Nieves J, et al. Two-year clinical outcome of 500 consecutive cases undergoing Descemet membrane endothelial keratoplasty. Cornea. 2017; 36:655-660.

Price MO, et al. Descemet's membrane endothelial keratoplasty: prospective multicenter study of visual and refractive outcomes and endothelial survival. Ophthalmology. 2009; 116:2361-2368.

Roberts HW, et al. Visual outcomes and graft thickness in microthin DSAEK-one-year results. Cornea. 2015; 34:1345-1350.

Rodriguez-Calvo-de-Mora M, et al. Clinical outcome of 500 consecutive cases undergoing Descemet's membrane endothelial keratoplasty. Ophthalmology. 2015; 122:464-470.

Romano V, et al. Preparation of ultrathin grafts for Descemet-stripping endothelial keratoplasty with a single microkeratome pass. J Cataract Refract Surg. 2017; 43:12-15.

Rudolph M, et al. Corneal higher-order aberrations after Descemet's membrane endothelial keratoplasty. Ophthalmology. 2012; 119:528-535.

Scorcia V, et al. Pentacam assessment of posterior lamellar grafts to explain hyperopization after Descemet's stripping automated endothelial keratoplasty. Ophthalmology. 2009; 116: 1651-1655.

Singh A, et al. Systematic review and meta-analysis of clinical outcomes of Descemet membrane endothelial keratoplasty versus Descemet stripping endothelial keratoplasty/ Descemet stripping automated endothelial keratoplasty. Cornea. 2017; 36:1437-1443.

Terry MA. Endothelial keratoplasty: why aren't we all doing Descemet membrane endothelial keratoplasty? Cornea. 2012; 31:469-471.

Tourtas T, et al. Descemet membrane endothelial keratoplasty versus Descemet stripping automated endothelial keratoplasty. Am J Ophthalmol. 2012; 153:1082-1090.e2.

Vira S, et al. Textural interface opacity after Descemet stripping automated endothelial keratoplasty: a report of 30 cases and possible etiology. Cornea. 2013; 32:e54-e59.

Kurji KH, et al. Comparison of Visual Acuity Outcomes Between Nanothin Descemet Stripping Automated Endothelial Keratoplasty and Descemet Membrane Endothelial Keratoplasty. Cornea. 2018; 37:1226-1231.

SYSTEMS AND METHODS FOR PREPARING CORNEAL TISSUE FOR IMPLANT

CROSS-REFERENCE TO RELATED APPLICATIONS

This application claims priority to, and benefit of, U.S. Provisional Patent Application Ser. No. 62/810,351, filed Feb. 25, 2019, the contents of which are incorporated entirely herein by reference.

FIELD OF THE INVENTION

The present disclosure pertains to systems and methods for preparing conical tissue for implant, and more particularly, to systems and methods for preparing conical tissue with a thickness of less than 100 µm (e.g., equal to or less than 50 µm) for implant.

BACKGROUND

Endothelial keratoplasty (EK) involves selectively replacing dysfunctional or diseased conical endothelium with donor endothelial grafts. EK procedures, such as Descemet membrane endothelial keratoplasty (DMEK) and Descemet stripping automated endothelial keratoplasty (DSAEK), have become the preferred treatment for endothelial dysfunction or disease. DMEK has grown in popularity because it provides true anatomic replacement of recipient diseased Descemet membrane and endothelium. Because DMEK does not involve any transfer of stromal tissue, however, tissue handling and graft unscrolling make it more technically challenging and potentially more unpredictable than DSAEK. As a result, DSAEK remains the most popular endothelial keratoplasty technique in the United States. However, overall visual acuity and rejection rates for DSAEK have been shown to be inferior when compared with DMEK.

SUMMARY

According to aspects of the present disclosure, embodiments can consistently achieve thicknesses of ≤50 µm for corneal tissue for DSAEK. Grafts with thicknesses of ≤50 µm are also known as nanothin DSAEK (NT-DSAEK) grafts. Evidence shows that using thinner DSAEK grafts, particularly NT-DSAEK grafts, can significantly improve visual outcomes, making the procedure more comparable to DMEK.

According to an example embodiment, a method for producing a corneal graft includes drying a donor cornea to cause a pre-cut thickness of the donor cornea to decrease. The method includes, concurrently with drying the donor cornea, determining pre-cut thickness measurements for the donor cornea. The method includes, in response to the pre-cut thickness measurements indicating the pre-cut thickness of the donor cornea has decreased to a predetermined value, cutting the donor cornea to a post-cut thickness of less than or equal to 100 µm to produce a corneal graft. In particular, the post-cut thickness may be less than or equal to 50 µm.

In the example embodiment, the donor cornea may be cut with a microkeratome with a selected microkeratome head. In some cases, the method further includes selecting the selected microkeratome head according to the decrease in the pre-cut thickness to the predetermined value. In yet other cases, the method further includes determining the predetermined value for the decrease in the pre-cut thickness according to the selected microkeratome head. In other cases, the method further includes selecting the selected microkeratome head from a plurality of different microkeratome heads. In further cases, the microkeratome may be a rotational style microkeratome.

In the example embodiment, the pre-cut thickness measurements may be determined with a pachymeter.

In the example embodiment, the method may further include removing an epithelium of the donor cornea to reduce the pre-cut thickness of the donor cornea further.

In the example embodiment, the method may further include determining a post-cut thickness measurement of the corneal graft.

In the example embodiment, the method may further include implanting the corneal graft according to Descemet stripping automated endothelial keratoplasty (DSAEK).

DESCRIPTION

Overall visual acuity and rejection rates for DSAEK have been shown to be inferior when compared with DMEK. This is often attributed to the fact that, in contrast to DMEK, DSAEK grafts retain a variable degree of stroma in addition to Descemet membrane and endothelium. Evidence suggests that minimizing the amount of residual stroma on a DSAEK graft and using thinner DSAEK grafts can significantly improve visual outcomes, making the procedure more comparable to DMEK. For instance, DSAEK grafts with a thickness of ≤131 µm have demonstrated better postoperative best-corrected visual acuity compared to DSAEK grafts with a thickness of >131 µm. As such, many DSAEK surgeons have become increasingly interested in using thinner grafts. Over time, as surgeons have grown more comfortable with handling thinner DSAEK grafts and insertion techniques have become more advanced, increasing demand has been placed on eye banks to provide these thinner grafts.

Target graft thicknesses have decreased from 70 µm to 100 µm to even thinner thicknesses of 70 µm. Grafts of such thicknesses are also known as ultrathin DSAEK (UT-DSAEK) grafts. The growing demand for UT-DSAEK grafts requires that eye banks have a reliable processing technique to cut these extremely thin grafts. Most DSAEK grafts processed in U.S. eye banks are cut to a targeted depth using a microkeratome. For instance, a microkeratome from Moria Inc. (Antony, France) applanates and cuts as it pivots over a cornea mounted on an artificial anterior chamber (AAC). The depth of the cut is largely determined by the various microkeratome heads available, which vary the height of the blade (in millimeters) from the applanated conical surface. Because of operator variability and variations of tissue biomechanics in deeper corneal stroma, the specific height of the blade in each microkeratome head does not accurately predict the depth of cut. As a result, cutting extremely thin DSAEK grafts can be challenging because of the risk of perforation from cutting too deeply.

According to aspects of the present disclosure, a single-pass technique for cutting extremely thin tissue employs an operator-specific nomogram to predict more accurately the cut depth for each of various microkeratome heads. With this technique, thicknesses of ≤50 μm can be achieved consistently. Grafts with thicknesses of ≤50 μm are also known as nanothin DSAEK (NT-DSAEK) grafts.

Figure 1:
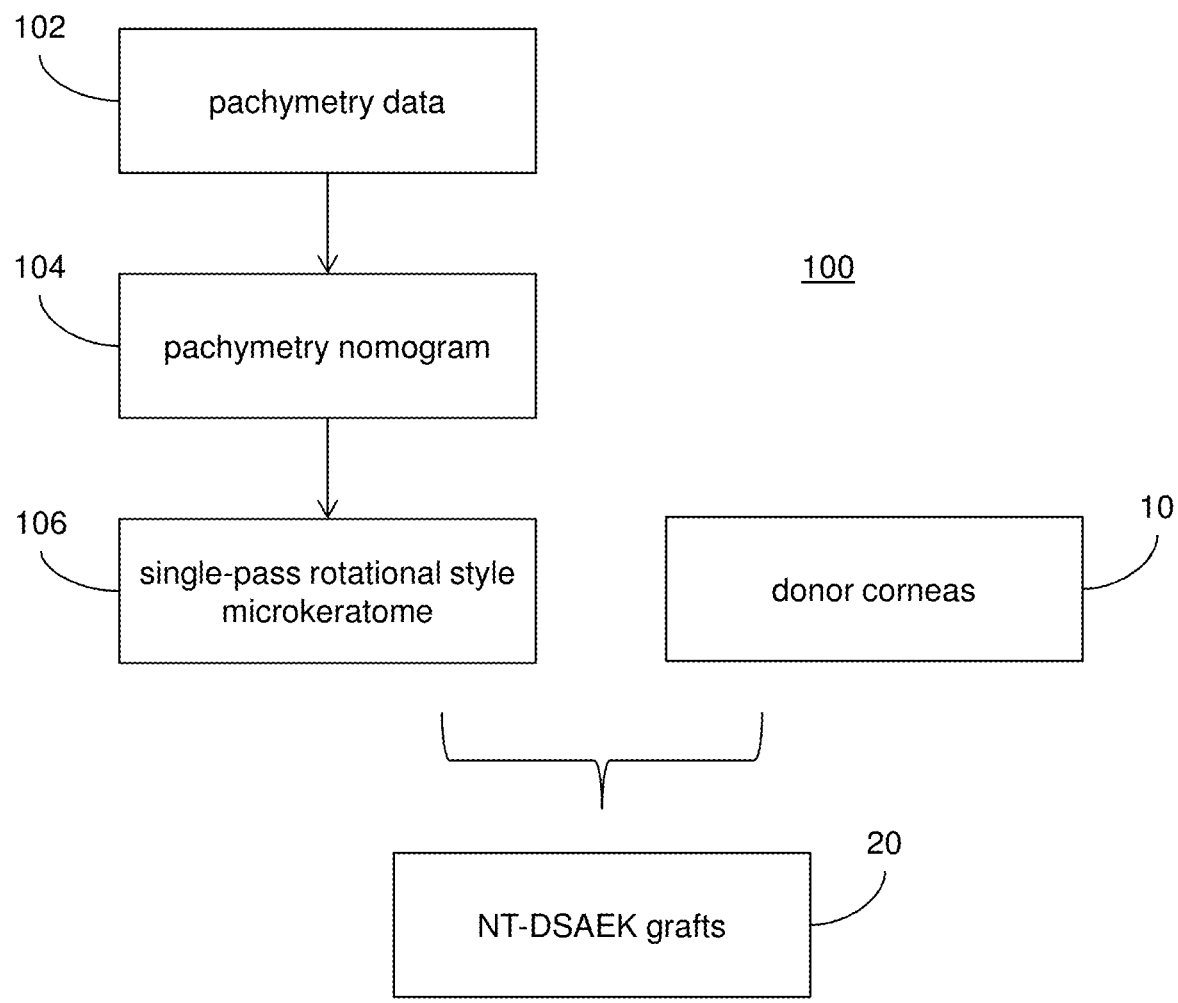
FIG. 1 illustrates an example system for producing grafts for corneal implant, according to aspects of the present disclosure.

FIG. 1 illustrates an example system 100 for producing DSAEK grafts 20, such as NT-DSAEK grafts with thicknesses of ≤50 μm. The example system 100 includes a pachymetry nomogram 104 (e.g., stored on and retrieved from computer-readable media) and a single-pass rotational style microkeratome 106, such as a Moria microkeratome. Using pachymetric data 102 from a plurality of DSAEK cuts performed over a period of time (e.g., approximately two years) by a particular technician with various microkeratome heads, an individualized pachymetry nomogram 104 can be generated for the particular technician and each microkeratome head. For instance, generation of the pachymetry nomogram 104 can begin with cut depth data 102 from approximately ten initial procedures. After each additional procedure, additional data 102 can then be added continuously over time with refinements to the cut depth predictions. Applying information from the pachymetry nomogram 104, the microkeratome 106 can cut donor corneas 10 to produce the DSAEK grafts 20.

Figure 2:
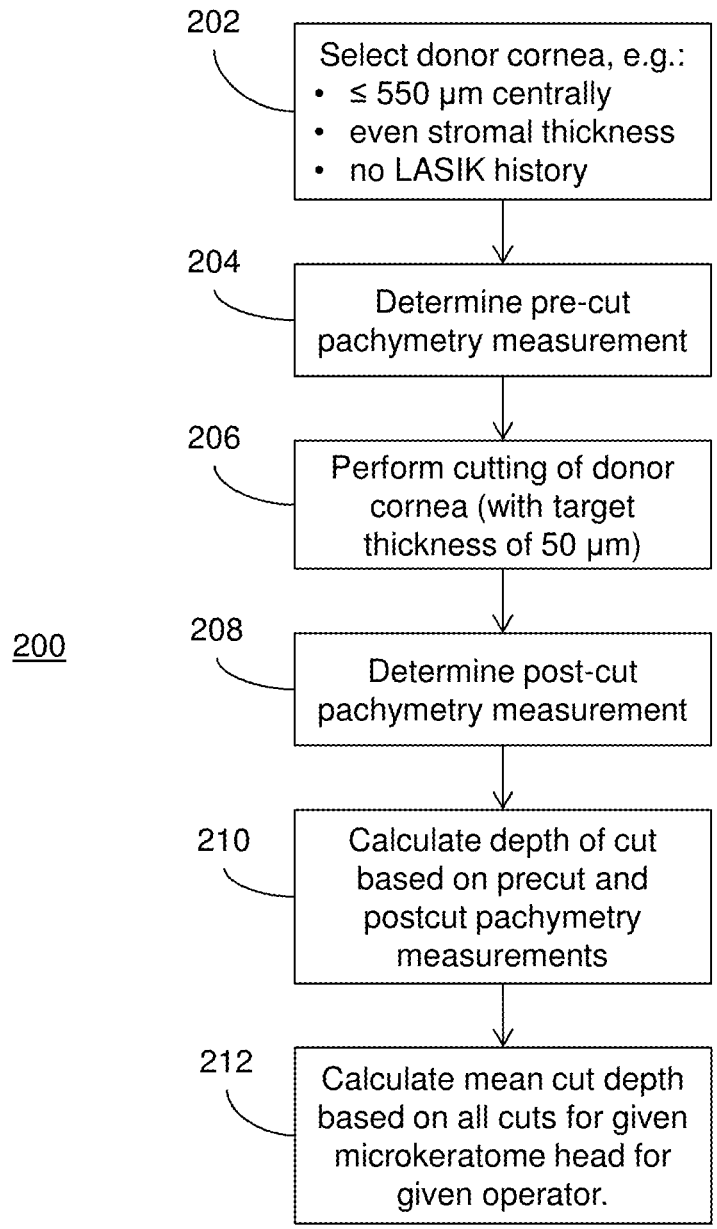
FIG. 2 illustrates an example procedure for producing grafts and generating a nomogram, according to aspects of the present disclosure.

FIG. 2 illustrates an example procedure 200 for producing DSAEK grafts and generating the nomogram 104 for operation of the microkeratome 106. In act 202, an appropriate donor cornea is selected to achieve a target thickness of ≤50 μm. In particular, it is preferable to employ a donor cornea that is ≤550 μm in thickness centrally. Deep microkeratome cuts can produce more variability in cut depth than shallow cuts due to the elasticity of the corneal stroma. Consequently, thinner corneas, which require less removal of tissue, are preferable when trying to achieve a small target thicknesses (e.g., ≤50 μm), with little margin for error. Variations in stromal thickness, either because of laser in situ keratomileusis (LASIK) or anterior scarring within the cutting area, can also create unpredictable and irregular cuts when producing the grafts. Therefore, preferably, the suitable donor cornea selected in act 202 has a substantially even stromal layer thickness and no history of LASIK.

In act 204, immediately before cutting of the selected donor cornea, pre-cut pachymetry measurement is determined intraoperatively. For instance, the donor cornea is first centered on a Moria AAC and mounted with storage medium backed by a constant 100 mm Hg of hydrostatic pressure from a balanced salt solution bottle hung at a fixed height above the work area. Loose epithelium is removed with eye spears wetted with balanced salt solution in cases in which the epithelium is irregular. In cases of slightly thicker corneas in which target graft thickness is unlikely to be achievable based on the predicted cut depth of even the deepest blade, the epithelium can be completely removed to thin the cornea. The pre-cut pachymetry data can then be obtained, for instance, via ultrasound pachymetry.

After the pre-cut pachymetry data is obtained in act 204, the cutting of the donor cornea is performed in act 206. For instance, with the donor cornea mounted on the Moria AAC described above, a single pass of the microkeratome blade 106 is performed. The tubing leading into the AAC is pinched and clamped with a hemostat to hold the pressure constant during the pass of the microkeratome blade 106. Four sterile ink marks may be added at cardinal points of the graft bed edge to help the surgeon center a trephine in the operating room. The anterior stromal cap is then replaced on the graft bed, and the cornea is placed in fresh storage media in a viewing chamber.

In act 208, a post-cut pachymetry measurement is determined. For instance, thirty minutes after act 206, final thickness for the graft is measured via optical coherence tomography (OCT) or specular microscopy. These two approaches for measuring final thickness correlate strongly with each other. In act 210, the depth of the cut is calculated according to the difference between the pre-cut and post-cut pachymetry measurements. The depth of cut is calculated for each graft produced according to acts 202, 204, 206, and 208. In act 212, a mean depth of cut is then calculated by averaging the results for all cuts. This can then be used as a predictive guide for the next expected depth of cut for the given microkeratome head in the hands of the given operator. The example procedure 200 can be repeated by the given operator for each of a single set of reusable microkeratome heads to generate a pachymetry nomogram as shown, for instance, as TABLE 1 (for a single operator using a single set of microkeratome heads). To generate a pachymetry nomogram for producing NT-DSAEK (or UT-DSAEK) grafts, act 206 above aims to cut the donor cornea to a thickness as close to 50 μm as possible.

Figure 3:
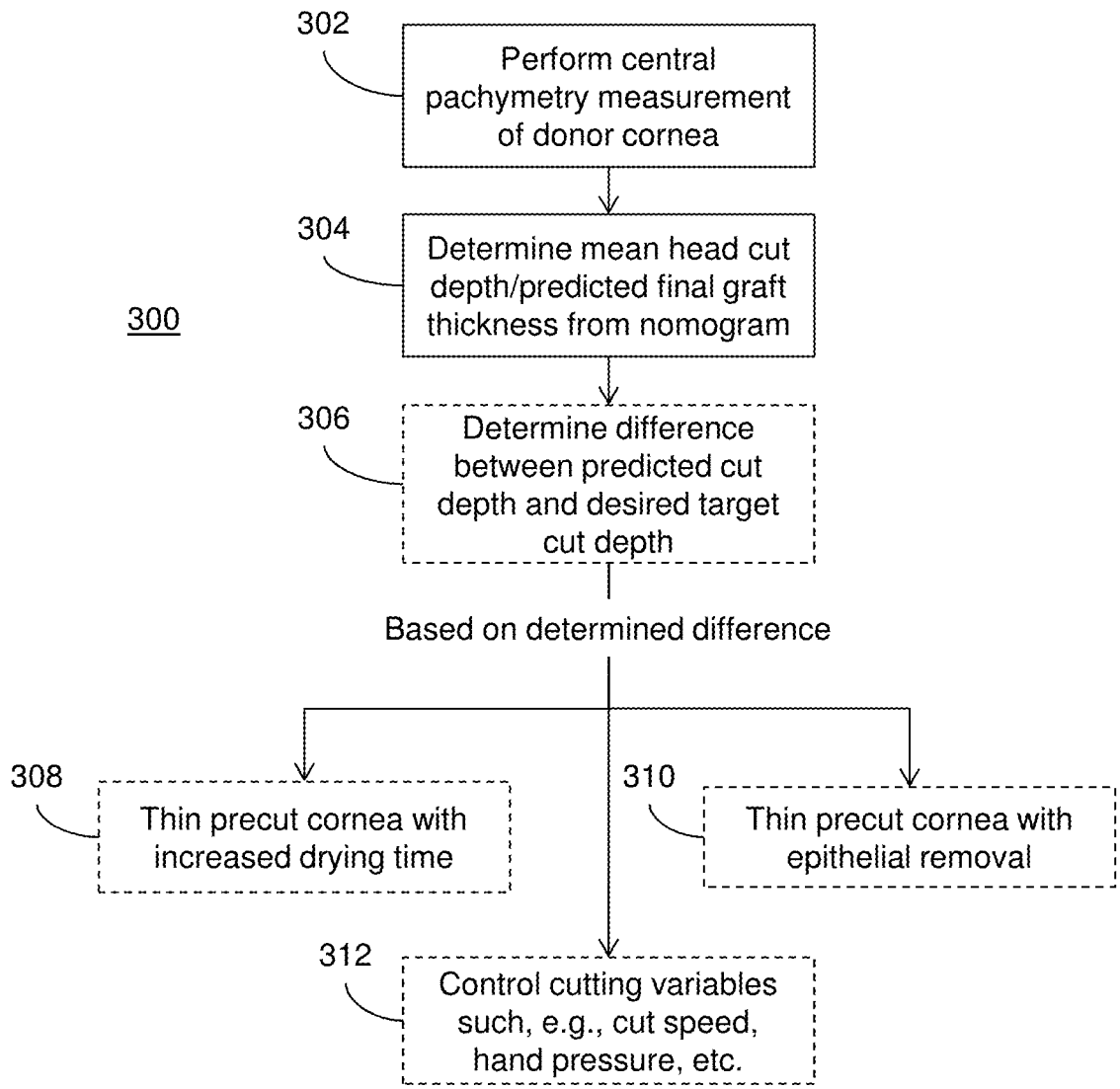
FIG. 3 illustrates an example procedure for achieving desired thicknesses for grafts, according to aspects of the present disclosure.

FIG. 3 illustrates an example procedure 300 for achieving desired thicknesses for DSAEK grafts, e.g., NT-DSAEK grafts. In act 302, a central pachymetry measurement of a donor cornea (e.g., mounted on an AAC) is determined. Using the central pachymetry measurement as input in act 304, a mean depth of cut and correspondingly a predicted final graft thickness are determined from a pachymetry nomogram as shown, for instance, in TABLE 1. In act 306, a difference between the predicted cut depth and the desired target cut depth may be determined. The difference can be addressed in act 308 by employing techniques to thin the pre-cut corneal thickness with increased drying time. Additionally or alternatively, the difference can be addressed in act 310 by employing techniques to thin the pre-cut corneal thickness with epithelial removal. Greater time on the AAC allows for tissue to thin by dehydration, which helps if the cornea is too thick for the nearest microkeratome head to achieve the target. Conversely, leaving the epithelium intact increases intraoperative thickness 15 μm to 30 μm relative to when it is removed. Additionally or alternatively, the difference can be addressed in act 312 by controlling additional cutting variables such as cut speed and hand pressure. Longer pass times and firmer hand pressure result in deeper than average cuts, creating thinner than average grafts for the given operator. A lighter hand pressure and faster pass will have the opposite effect. It may be important to observe the epithelium just before the microkeratome cut because exposure can give focal irregular areas. In addition, younger donors have more pliable stroma and therefore tend to become thinner with the same head than older donors. Using these variables alone or in combination greatly assists in closing any differences between predicted cut depths and desired target cut depths.

TABLE 1

Sample Nomogram for Ultrasound Pachymetry-
Single Set, Single Operator

| Intraoperative Pachymetry Values, μm | Microkeratome head (Mean cut depth, μm) | | |
|---|---|---|---|
| | 250 (310) | 300 (375) | 350 (464) |
| | Predicted Residual Bed Thickness, μm | | |
| 400 | 90 | 25 | −64 |
| 425 | 115 | 50 | −39 |
| 450 | 140 | 75 | −14 |
| 475 | 165 | 100 | 11 |
| 500 | 190 | 125 | 36 |
| 525 | 215 | 150 | 61 |
| 550 | 240 | 175 | 86 |

Figure 4:
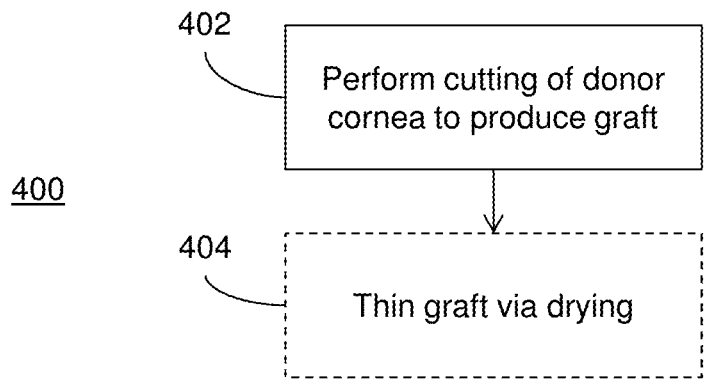
FIG. 4 illustrates an example procedure for reducing thickness of a graft, according to aspects of the present disclosure.

Due to variations between individual operators (e.g., operator setup time (which may result in time for graft dehydration), hand size, and physical strength), it is difficult to make a standardized, generic nomogram that applies to all operators. An individualized nomogram, however, based on many previous cuts accounts for individual variations and allows for accurate selection of microkeratome heads for each operator. As described above, it is typically more challenging to achieve grafts with ≤50 μm when starting with thicker corneas (as thinner corneas typically fall into the nomogram). To compensate in these cases, additional variables can be adjusted after using the individualized nomogram. For instance, the graft is allowed to dehydrate for a period of time while mounted on an AAC. The graft can remain on the AAC for up to five minutes to decrease the graft thickness by an additional total of 20 to 30 μm. During this period, the graft can be checked every minute in case the target thickness is achieved in less than five minutes. FIG. 4 illustrates an example procedure 400 where the graft is dried to reduce its thickness in act 404 after the donor cornea is cut to produce the graft in act 402. In some embodiments, the example procedure 400 may be performed after the example procedure 300 shown in FIG. 3.

An experienced operator can develop a consistent standard cut (with his/her own standard speed and weight/firmness) 95% to 99% of the time. An experienced operator can also develop a consistent deeper cut (e.g., with slower speed and increased weight/firmness) to obtain a deeper cut of approximately 20 μm to 30 μm. With these two consistent cuts, an operator can produce a meaningful nomogram even when deeper cuts are necessary. Combining these additional variables allows thicknesses for NT-DSAEK grafts to be achieved more consistently.

Additionally, rather than targeting a range of thicknesses for cutting the graft (e.g., 50 μm-90 μm), operators achieve greater accuracy by targeting a specific thickness value (e.g., 50 μm). As such, success is not determined by falling into the targeted thickness range but by falling within a standard deviation from the specific thickness value. In one aspect, this approach forces operators to focus more greatly on accuracy for every cut. Furthermore, operators also achieve greater accuracy when paying attention to corneal curvature.

Figure 5:
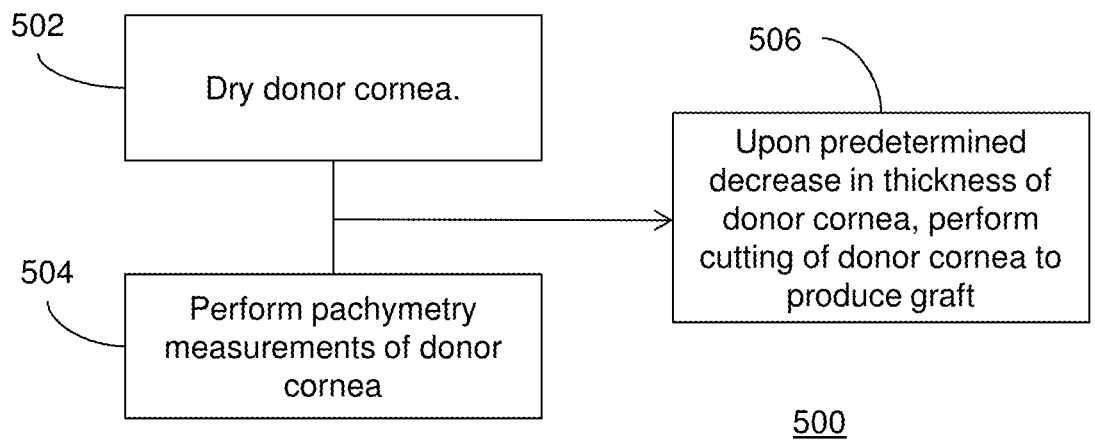
FIG. 5 illustrates another example procedure for achieving a desired thickness for a graft, according to aspects of the present disclosure.

The present inventors have determined that greater accuracy for cutting thinner grafts is achieved by allowing the donor cornea to dry and decrease in thickness by a predetermined amount prior to cutting. For instance, an operator can wait until a donor cornea dries to a thickness of 500 μm and employ a microkeratome head of 350 μm to achieve a desired thickness, or the operator can wait until the donor cornea dries to a thickness of 400 μm and employ a microkeratome head of 300 μm. Thus, FIG. 5 illustrates an example procedure 500 where the donor cornea is allowed to dry and decrease in pre-cut thickness in act 502 and a pachymeter is concurrently employed in act 504 to measure and monitor the pre-cut thickness of the donor cornea as it dries. Once the pre-cut thickness of the donor cornea has decreased by a predetermined amount, the donor cornea can be cut in act 506 to produce a graft (e.g., NT-DSAEK graft). In some embodiments, the epithelium may be removed to reduce the thickness of the donor cornea further prior to act 506.

A microkeratome as discussed above may be employed to the cut the donor cornea in act 506. In some cases, a particular microkeratome head may be selected from a plurality of possible microkeratome heads according to the decrease in the pre-cut thickness. In other cases, the decrease in the pre-cut thickness may be determined according to a prior selection of a particular microkeratome head.

The amount of desired drying and decrease in thickness may be determined according to the pachymetry nomogram for the given operator. As described above, in the example procedure 300, the difference between the predicted cut depth and the desired target cut depth can be addressed in act 308 by employing techniques to thin the pre-cut corneal thickness with increased drying time. For instance, according to the pachymetry nomogram in TABLE 1, the given operator can wait until a donor cornea dries to a thickness of 425 μm prior to employing a microkeratome head of 300 μm, which produces a mean cut depth of 375 μm for the given operator, to achieve a predicted thickness of 50 μm for a NT-DSAEK graft.

To assess what impact cutting NT-DSAEK has on corneal endothelium, tissue data for all DSAEK and DMEK grafts distributed by an eye bank over a two-year period were reviewed. DSAEK grafts were separated into three groups based on graft thickness: grafts with thicknesses of ≤50 μm were included in a NT-DSAEK group; grafts with thicknesses ranging from 51 μm to 70 μm were included in a first UT-DSAEK group; and grafts with thicknesses ranging from 71 μm to 100 μm were included in a second UT-DSAEK group. Mean pre-cut and post-cut endothelial cell counts (ECCs) were then calculated for each of the DSAEK groups and for all DMEK grafts distributed by the eye bank over the course of the study period. For statistical analysis, the normality of data was tested with D'Agostino-Pearson normality tests. Based on the normality of data, analysis of variance or Kruskal-Wallis is used to determine whether there is a statistically significant difference among the groups. If there is significance, the t test is used to compare the groups pairwise. $P<0.05$ is considered statistically significant. Endothelial cell loss (ECL) is also evaluated using calcein AM stains, and images are analyzed using ImageJ Trainable Weka Segmentation plugin (National Institutes of Health; http://rsbweb.nih.gov/ij/).

To calculate the efficacy of a nomogram for cutting NT-DSAEK grafts, all outcomes from attempted NT-DSAEK preparations for planned surgical distribution for a two-year period were identified and reviewed. In all cases, careful selection of appropriate donor corneas was performed as described above. Final graft thickness from all cuts was evaluated. Outcomes, including endothelial perforation or unacceptable endothelial damage after processing, were also documented. Tissue loss rates were then calculated and compared with tissue loss rates for DMEK and DSAEK.

Over two years, the eye bank distributed a total of 39 DSAEK grafts for surgical transplantation that, intentionally or unintentionally, had a final thickness of ≤50 µm after being prepared with a single-pass microkeratome technique. Mean final graft thickness for these NT-DSAEK grafts was 41.0 µm±6.4 µm (range 26 µm to 50 µm). TABLE 2 demonstrates the post-processing ECC outcomes for these NT grafts compared with other DSAEK and DMEK grafts that were distributed by the eye bank over that same period. For NT-DSAEK tissue, mean ECC was 2726 before cutting and 2814 after cutting. This was similar to pre-processing and post-processing ECCs for UT-DSAEK (both at 51 µm to 70 µm thickness and at 71 µm to 100 µm thickness) and DMEK grafts. Mean ECC (before and after) did not differ in NT-DSAEK, UT-DSAEK, and DMEK grafts (P=0.759 and 0.633, respectively). Pairwise comparisons between each DSAEK group and the DMEK group are shown in TABLE 2.

processing. Calcein AM is not visible in dead cells but fluoresces green when cleaved by active cellular metabolism. The images were also analyzed using ImageJ Trainable Weka Segmentation plugin to quantify total ECL. After an NT-DSAEK cut, the cornea exhibits additional central cell loss and peripheral cell loss. The preprocessing baseline of 2% ECL increases to 5% after the microkeratome cut with a focal area of ECL.

Evidence correlates thinner DSAEK grafts with better visual acuity. The first multicenter, prospective, double-masked, randomized, controlled clinical trial demonstrated that UT-DSAEK (mean 101 µm) results in faster and better recovery of best-corrected visual acuity with similar refractive outcomes, ECL, and incidence of complications compared with DSAEK (mean 209 µm).

Quality of vision may also be improved with thinner DSAEK grafts. Graft thickness correlates with graft asymmetry, which in turn may be associated with higher-order aberrations. Besides graft thickness, factors such as stromal scarring, interface opacity, graft shape, posterior curvature, and total corneal thickness may play a role in poor visual

TABLE 2

Endothelial Cell Count Comparison by Graft Thickness

|  | NT-DSAEK (≤50 µm) | UT-DSAEK (51-70 µm) | Other UT-DSAEK (71-100 µm) | DMEK |
| --- | --- | --- | --- | --- |
| Grafts (n) | 39 | 119 | 257 | 453 |
| Mean thickness, µm | 41.0 ± 6.4 | 61.0 ± 5.7 | 88.8 ± 8.7 | NA |
| Mean ECC before microkeratome | 2726 ± 296.5 | 2772 ± 326.9 | 2742 ± 279.4 | 2728 ± 268.3 |
| Mean ECC after microkeratome | 2814 ± 333.7 | 2772 ± 298.3 | 2789 ± 291.7 | 2800 ± 272.5 |
| P* | 0.991 | 0.777 | 0.961 | NA |

ECC, endothelial cell counts; DMEK, Descemet membrane endothelial keratoplasty; DSAEK, Descemet stripping automated endothelial keratoplasty; NA, no applicable, NT-DSAEK, nanothin DSAEK; UT-DSAEK, ultrathin DSAEK.
*P value of pairwise comparison of mean ECC after microkeratome to DMEK.

Over the two year period, there were twenty-one intentional attempts to cut NT-DSAEK grafts for transplantation (based on surgeon request). The graft processing outcomes are displayed in TABLE 3. The overall tissue loss rate was 4.8% (1/21). In comparison, the overall DSAEK (all types, n=610) and DMEK (n=236) tissue loss rates were 3.6% and 2.9%, respectively, over the past 12 months. All nonperforated grafts had acceptable endothelium for transplantation. Of the nonperforated corneas, there was a 60% (12/20) success rate for obtaining thickness of ≤50 µm. In terms of final graft thickness for the processed tissue cuts, 85% (17/20) achieved thicknesses of ≤51 µm to 70 µm and 100% (20/20) achieved thicknesses of ≤71 µm to 100 µm.

TABLE 3

|  | NT-DSAEK (≤50 µm) |
| --- | --- |
| NT requests | 16 |
| No. tissue loss | 1 |
| Loss rate/request | 6.3% (1/16) |
| No. tissue cuts to fulfill requests | 21 |
| Total no. tissue loss | 1 |
| Loss rate/cut | 4.8% (1/21) |
| No. tissue in NT range | 12 |
| NT (≤50 µm) success rate/processed cuts | 60.0% (12/20) |
| UT (51-70 µm) success rate | 85.0% (17/20) |
| UT (70-100 µm) success rate | 100.0% (20/20) |

DSAEK, Descemet stripping automated endothelial keratoplasty; NT, nanothin; NT-DSAEK, nanothin Descemet stripping automated endothelial keratoplasty; UT, ultrathin.

NT-DSAEK tissue was also stained with calcein AM to highlight representative cell loss before and after DSAEK outcomes in DSAEK. Although it may improve with time, irregularity or stromal scarring at the anterior graft surface may also limit visual function. Thus, thinner grafts with minimal stromal substance may enhance graft symmetry, regularity of shape, and quality of vision. Microkeratome-assisted DSAEK graft preparation has led to increased reproducibility and improved quality/smoothness of the stromal surface.

Advantageously, UT- and NT-DSAEK employ similar surgical techniques for graft insertion and positioning as traditional DSAEK. This translates to more predictable operating room time. DSAEK detachment rates are potentially lower than those of DMEK. NT-DSAEK appears to be a viable option that is comparable to DMEK. Other UT techniques have used air drying, continuous drying with polyvinyl alcohol sponges, controlling AAC pressure, and using a THIN-C medium to reduce donor corneal thickness before a single microkeratome pass. Alternatively, the double-pass microkeratome technique has been used to achieve UT tissue with a second microkeratome pass after a standard single-pass microkeratome cut. Each of these techniques uses a tailored nomogram. A single-pass may be safer and less detrimental compared with a double-pass technique. Microkeratome-related complications (7.2%), such as buttonholing and perforation, occurred during the second pass. Endothelial cell damage is more likely with the double-pass technique. The double-pass technique involves a longer duration of raised intraocular pressure and the risk of obtaining a smaller diameter cut after the second pass.

A limitation of microkeratome dissection can be its poor accuracy in consistently determining the final thickness of the DSAEK graft. However, using the nomogram-guided single-pass technique disclosed herein allows thinner graft thicknesses to be achieved consistently manner. This technique may involve manipulating multiple variables based on the final graft thickness predicted by the nomogram. The presented nomogram can be even further refined by including more variables (i.e., hand pressure, speed, etc.).

Formulating a personalized nomogram for each technician requires multiple previous cuts and careful analysis of the data. Each nomogram is continually changing as additional cuts are added for analysis. With additional cuts for the NT-DSAEK grafts, a nomogram can be further refined.

In conclusion, the customized, single-pass microkeratome nomogram described above allows for standardized creation of NT-DSAEK grafts. Although the cuts may be deep (final graft thickness as thin as 26 mm), the procedure seems to be safe for endothelial cells. The tissue loss rate in the study above was very low, measuring 4.8%, whereas the chance of achieving target thickness was 60%. All the tissue cuts that were not within the NT-DSAEK range were still within the UT-DSAEK range.

A recent study compared the visual outcomes and complications between NT-DSAEK and DMEK. A prospective comparative case series was performed patients undergoing NT-DSAEK or DMEK alone or in combination with cataract surgery. Exclusion criteria were any concurrent ocular co-morbidities: any macular pathology, moderate or advanced glaucoma, amblyopia, and any previous corneal pathology other than that related to Fuchs dystrophy. The parameters measured included demographics, preoperative diagnosis, preoperative and corresponding postoperative best spectacle-corrected visual acuity (BSCVA), and intraoperative and postoperative complications. Data were collected at a preoperative evaluation and subsequent follow-up examinations at postoperative month 1, postoperative month 3, postoperative month 6, and postoperative month 12. Visual acuity was assessed using a computerized system (Smart System; M&S Technologies, Skokie, Ill.). Postoperative graft thickness was measured using anterior segment optical coherence tomography (Visante; Carl Zeiss Meditec, Inc, Dublin, Calif.).

All NT-DSAEK surgeries were performed by a single surgeon. Preoperatively, on the day of surgery, inferior laser peripheral iridotomy was performed. When combined with cataract surgery, the cataract portion was completed first through a clear corneal incision. Cohesive viscoelastic was then inserted into the anterior chamber, and Descemet membrane was stripped using a reverse Sinskey hook (Storz Ophthalmic Instruments, St. Louis, Mo.). After removal of the viscoelastic with irrigation-aspiration, the clear corneal incision was enlarged to 4.0 mm before tissue insertion. All grafts were inserted into the anterior chamber using the EndoSerter (SightLife Surgical, Seattle, Wash.). The anterior chamber was then completely filled with air with the intraocular pressure of approximately 40 to 50 mm Hg, and the patient was observed for 10 minutes. After 10 minutes, partial air-fluid exchange was performed, leaving approximately an 80% air bubble. The patient was instructed to remain in the supine position as much as possible until the postoperative day 1 visit.

All DMEK surgeries were performed by another single surgeon. Briefly, inferior laser peripheral iridotomy was performed at least 1 day before surgery in all eyes. If combined with cataract surgery, cataract surgery was first completed, followed by injecting of an acetylcholine intraocular solution to constrict the pupil. A cohesive viscoelastic was inserted into the anterior chamber, and an 8.0-mm diameter descemetorhexis was created using an inverted Sinskey hook (D.O.R.C. International BV). Intraoperatively, the donor corneoscleral button was trephined, and the donor Descemet scroll was stained with trypan blue 0.06% solution (VisionBlue; Dutch Ophthalmic USA, Exeter, N.H.) for 30 seconds. Using a 1CART30 (Abbott Medical Optics, Santa Ana, Calif.) intraocular lens cartridge injector connected to a 1-mL syringe, tissue was drawn up and inserted into the anterior chamber. After shallowing the anterior chamber, the graft was oriented endothelial side down and gently unfolded with bimanual cannula tapping motions. A 20% SF6 bubble was injected under the donor graft to position the tissue against the recipient's posterior stroma. The anterior chamber was then completely filled with the SF6 for 10 minutes with an intraocular pressure of approximately 40 to 50 mm Hg. At the completion of the 10 minutes, SF6-fluid exchange was performed to pressurize the eye, leaving the eye with an 80% bubble. Postoperatively, patients were administered topical fluoroquinolones for 1 week and topical steroids, which were tapered routinely postoperatively.

For statistical analysis, the measured Snellen visual acuity was converted to logarithm of the minimum angle of resolution (log MAR) visual acuity. Statistical analysis was performed using SPSS version 21 (SPSS, Inc, Chicago, Ill.). Data were presented as mean 6 SD, and the level of significance was 0.05. To compare collected and baseline data, $x^2$ or Fisher exact tests were used for qualitative data. The t test was used for quantitative data. To compare results between groups, the independent t test or Mann-Whitney U test was used based on normality test results.

During the study period, the first 28 consecutive eyes in each of the NT-DSAEK and DMEK groups that fulfilled the inclusion and exclusion criteria were included. A total of 28 eyes of 26 patients were included in each of the NT-DSAEK (61% females and 39% males) and DMEK (64% females and 36% males) groups. A total of 14 and 18 eyes underwent combined cataract surgery with DMEK or NT-DSAEK, respectively. Mean age for the eyes included in each group was 67.1 6 7.8 years and 67.6 6 13.9 years for NT-DSAEK and DMEK, respectively. Fuchs dystrophy was the underlying diagnosis in all eyes. Mean thickness of NT-DSAEK grafts was 41.0 6 7.5 mm (range: 26-50 mm). Demographics of each group are summarized in TABLE 4. Age, sex, T1 preoperative mean log MAR BSCVA, and median follow-up length were not found to be statistically significant between both groups.

TABLE 4

| Preoperative Variable | NT-DSAEK | DMEK | P* |
|---|---|---|---|
| Mean age (yr) | 67.1 | 67.6 | 0.86 |
| Sex (female/male) | 17/11 | 18/10 | >0.999 |
| CCT (μm) | 643.9 + 87.8 | 629.2 + 62.2 | 0.49 |
| BSCVA (logMAR) | 0.32 ± 0.16 | 0.33 ± 0.19 | 0.854 |
| Mean graft thickness (μm) | 41.0 ± 7.5 | NA | NA |

CCT, central corneal thickness; ECC, endothelial cell counts; NA, not applicable.
*P value of pairwise comparison between NT-DSAEK and DMEK.

Figure 6:
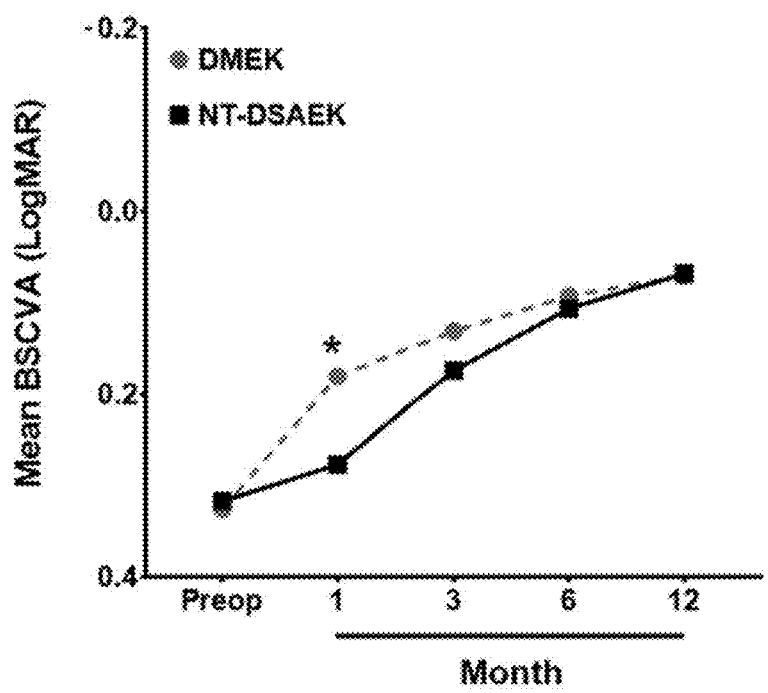
FIG. 6 illustrates a graph comparing postoperative BSCVA obtained after NT-DSAEK and DMEK procedures performed in an example study.

Preoperative mean log MAR BSCVA was not statistically significant between the NT-DSAEK [0.32±0.16 (20/42)] and DMEK [0.33±0.19 (20/43)] groups (P=0.854). At 1 month postoperatively, the DMEK group had significantly better mean BSCVA vision than the NT-DSAEK group [DMEK 0.18±0.20 log MAR (20/33) vs. NT-DSAEK 0.28±0.16 log MAR (20/40); P=0.049]. However, by 3 months postoperatively, this significant difference dissipated [DMEK 0.13±0.17 log MAR (20/27) vs. NT-DSAEK 0.17±0.12 log MAR (20/30); P=0.31], and both groups had comparable vision throughout the remainder of the postoperative period as shown in FIG. 6. At both 6 and 12 months, no significant difference in mean BSCVA was observed in either group [6 months: NT-DSAEK 0.11+0.10 log MAR (20/26) vs. DMEK 0.09+0.10 (20/25), P=0.63; 12 months: NT-DSAEK 0.07+0.09 log MAR (20/24) vs. DMEK 0.07+0.11 log MAR (20/24), P=0.95].

Figure 7:
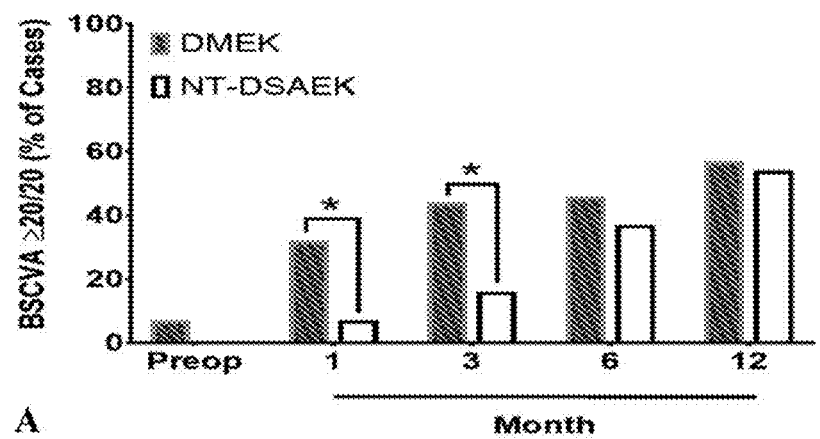
FIG. 7 illustrates a bar graph showing the distribution of best spectacle-corrected visual acuity after NT-DSAEK procedures performed in an example study.
Figure 7:
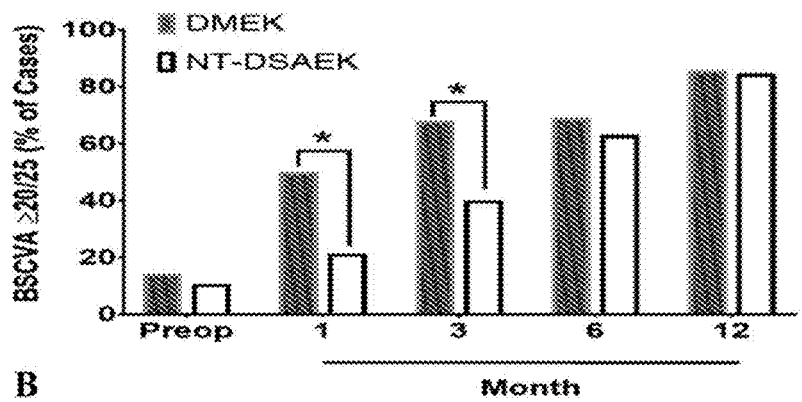

Overall, 93% of eyes in both NT-DSAEK and DMEK groups observed an improvement in visual acuity after surgery. There were no eyes in either group that experienced worsening of visual acuity compared with their preoperative BSCVA. At the last postoperative visit, 86% of DMEK and 85% of NT-DSAEK eyes achieved greater than or equal to 0.09 log MAR BSCVA (20/25) (P. 0.999), whereas 57% of DMEK and 54% of NT-DSAEK eyes achieved 0 log MAR BSCVA (20/20) (P. 0.999) as shown in FIG. 7.

No intraoperative complications were encountered in either group. Postoperatively, there were no cases of primary graft failure or graft rejection in either NT-DSAEK or DMEK groups. One eye in the NT-DSAEK group developed complete detachment at 1 week postoperatively, but after a successful rebubble, this eye maintained 0 log MAR BSCVA (20/20) at the last follow-up visit. No other graft dislocations or detachments were seen in either group. Furthermore, no episodes of endothelial graft rejection or failure were observed in either group.

The mean BSCVA was significantly better in the DMEK group at 1 month. However, by 3 months, the mean BSCVA was comparable between the DMEK and NT-DSAEK groups, and there was no significant difference throughout the remainder of the study. After 12 months, the percentage of patients in either group achieving mean log MAR BSCVA≥0.09 (Snellen equivalent, 20/25) was similar.

Recently, a systematic review and meta-analysis that compared the clinical outcomes of DMEK versus DSAEK concluded that DMEK provided superior visual acuity outcomes compared with DSAEK. However, many of the reviewed studies comparing DMEK with DSAEK were retrospective and did not attempt to standardize the thickness of tissues used in DSAEK; grouping thick DSAEK grafts with thinner DSAEK grafts likely skewed the results in favor of DMEK. In fact, previous work with thinner DSAEK tissues have shown improved visual acuity results with thinner DSAEK grafts. It has been demonstrated that the visual acuity curves for UT-DSAEK and DMEK essentially overlapped for the entire follow-up period, whereas the curve for conventional DSAEK remained at a lower level. Similarly, the recent study observed that after the initial postoperative 1-month visit, the visual acuity curves for NTDSAEK and DMEK were identical as shown in FIG. 6. Given the wide range of DSAEK graft thicknesses in the literature, it is unfair to compare the visual outcomes of DMEK with those of thicker versions of DSAEK. Rather, the focus should shift to comparing DMEK with thinner versions of DSAEK.

Despite what many authors believe, 20/20 vision is attainable with DSAEK. At 1 year, 57% of the NT-DSAEK patients in the recent study described above obtained 20/20 vision, which is higher than the value reported in previous studies on DSAEK (13.9%) and UT-DSAEK (39.5%), and equivalent to the DMEK patients (57%) in the recent study. These NT-DSAEK visual acuity results are also comparable to other previous DMEK outcomes. The results provide evidence that obtaining percentages of patients with 20/20 vision comparable to DMEK is possible with NT-DSAEK.

DMEK provides near-perfect anatomic replacement of the posterior recipient cornea, which many have attributed to the superior visual acuity outcomes of DMEK. Given the comparable results above between NT-DSAEK and DMEK, other factors in addition to an irregular nonanatomic stromal interface (attributed to graft thickness and asymmetry), posterior curvature, and total cornea aberrations may be responsible for limiting vision. One possibility for falling short of 20/20 vision in otherwise healthy eyes may include the severity of preoperative conical edema causing subepithelial fibrosis and disorganization of the internal stromal collagen fibers.

With respect to postoperative complication rates, the recent study above showed that DMEK and NT-DSAEK are equivalent. Although only 1 NT-DSAEK patient (3.6%) underwent a successful rebubbling procedure for complete graft detachment, the rate of rebubbling is similar or lower than that reported in studies published for DMEK and UT-DSAEK. In DSAEK grafts, air reinjection or rebubbling procedures are required only if the graft is detached entirely and free-floating in the anterior chamber because many partial DSAEK detachments have been observed to attach spontaneously without intervention. Furthermore, the decreased amount of stromal tissue resulting in a thinner and lighter graft may account for the decreased rate of rebubbling observed with NT-DSAEK compared with UT-DSAEK or conventional DSAEK. Conversely, in DMEK, air injections are typically performed for partial graft detachments. There were no postoperative complications in the DMEK series (no rebubbling or air injection procedures). It is noted that the rate of rebubbling or air injection procedures with DMEK has been shown to decrease with increased surgical experience and standardization of the procedure.

The higher rate of endothelial graft rejections reported for DSAEK compared with DMEK is believed to stem from varying amounts of residual stromal tissue associated with a wide variety of thicknesses of DSAEK donor tissues. For thicker versions of DSAEK, the reported average endothelial graft rejection rate is approximately 10%. However, when thinner versions of DSAEK (UT-DSAEK) are considered, the graft rejection rate is much lower at 2.8% at 1 year. Conversely, the 1-year rejection rate for DMEK has been found to vary from 0% to 5.7%. In the recent study above, the rate of endothelial graft rejection was found to be 0% for both NT-DSAEK and DMEK at 1 year. Therefore, the results further support the idea that compared with DMEK, thinner versions of DSAEK have similar low rates of immunologic rejection.

Despite the increased numbers of DMEK procedures being performed since 2012, DSAEK is still the procedure of choice for EK. Like UT-DSAEK, the advantages of NT-DSAEK include the similar and predictable surgical technique for graft insertion and positioning as seen with traditional DSAEK as described above. This translates to a more predictable operating room time, whereas in DMEK, additional time is often required for graft insertion, unscrolling, and achieving correct orientation of the graft. Furthermore, unlike DMEK, NT-DSAEK can be used in all complex cases without reservations (e.g., opaque corneas with poor visibility, in eyes with concurrent glaucoma filtering tubes or anterior chamber IOL, or aphakia).

Accordingly, the presented data support the notion that thinner tissue is paramount to optimizing visual results in EK. Compared with DMEK, NT-DSAEK produces comparable visual acuity outcomes and postoperative complications rates. Although DMEK still allows for quicker visual recovery, NT-DSAEK provides all EK surgeons a viable alternative that affords the same comfort and predictability as conventional DSAEK, but with visual outcomes that parallel DMEK.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the present disclosure. It is also contemplated that additional embodiments according to aspects of the present disclosure may combine any number of features from any of the embodiments described herein.

What is claimed is:

1. A method for producing a corneal graft, comprising:
   using an operator-specific nomogram to determine a predicted cut depth for a donor cornea;
   determining a predetermined value based on a difference between the predicted cut depth and a desired cut depth;
   drying the donor cornea to cause a pre-cut thickness of the donor cornea to decrease;
   concurrently with drying the donor cornea, determining pre-cut thickness measurements for the donor cornea; and
   in response to the pre-cut thickness measurements indicating the pre-cut thickness of the donor cornea has decreased by the predetermined value, cutting the donor cornea to a post-cut thickness of less than or equal to 100 μm to produce the corneal graft,
   wherein the donor cornea is cut with a single-pass rotational style microkeratome with a selected microkeratome head,
   wherein the operator-specific nomogram uses data to generate the predicted cut depth, the data including a plurality of donor cornea cuts by an operator technician using the selected microkeratome head, wherein the data for each of the plurality of donor cornea cuts of the donor cornea includes a pre-cut thickness measurement taken immediately before cutting and a post-cut thickness measurement of the corneal graft,
   wherein the operator-specific nomogram generates the predicted cut depth based on an average of the cut depths for the plurality of donor cornea cuts, wherein a cut depth for each of the plurality of donor cornea cuts is the difference between the pre-cut thickness measurement of the donor cornea and the post-cut thickness measurement.

2. The method of claim 1, further comprising selecting the selected microkeratome head according to the predetermined value.

3. The method of claim 1, further comprising determining the predetermined value for the decrease in the pre-cut thickness according to the selected microkeratome head.

4. The method of claim 1, further comprising selecting the selected microkeratome head from a plurality of different microkeratome heads.

5. The method of claim 1, wherein the post-cut thickness is less than or equal to 50 μm.

6. The method of claim 1, wherein the pre-cut thickness measurements are determined with a pachymeter.

7. The method of claim 1, further comprising removing an epithelium of the donor cornea to reduce the pre-cut thickness of the donor cornea further.

8. The method of claim 1, further comprising determining a post-cut thickness measurement of the corneal graft.

9. The method of claim 1, further comprising implanting the corneal graft according to Descemet stripping automated endothelial keratoplasty (DSAEK).

10. The method of claim 1, further comprising drying the donor cornea to cause the post-cut thickness of the donor cornea to decrease.

11. The method of claim 1, further comprising controlling one or more cutting variables during the cutting of the donor cornea to address the difference between the predicted cut depth and the desired cut depth.

12. The method of claim 1, further comprising using the operator-specific nomogram to determine an amount of desired drying and decrease in the pre-cut thickness of the donor cornea.

13. The method of claim 1, wherein the operator-specific nomogram generates a predicted graft thickness, wherein the predicted graft thickness is the difference between the pre-cut thickness measurement and the average of the cut depths.

14. The method of claim 1, wherein the operator-specific nomogram continuously updates the data after each corneal graft is produced.

* * * * *